(12) United States Patent
Napoletano et al.

(10) Patent No.: US 6,340,684 B1
(45) Date of Patent: Jan. 22, 2002

(54) PHTHALAZINE DERIVATIVES AS PHOSPHODIESTERASE 4 INHIBITORS

(75) Inventors: Mauro Napoletano, Milan; Gabriele Norcini, Vizzola Ticino; Giancarlo Grancini, Nova Milanese; Franco Pellacini, Milan; Gabriele Morazzoni, Lainate, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/764,983

(22) PCT Filed: Jul. 16, 1999

(86) PCT No.: PCT/EP99/05068

§ 371 Date: Jan. 22, 2001

§ 102(e) Date: Jan. 22, 2001

(87) PCT Pub. No.: WO00/05219

PCT Pub. Date: Feb. 3, 2000

(30) Foreign Application Priority Data

Jul. 21, 1998 (IT) .......................... MI98A1671

(51) Int. Cl.[7] .................. A61K 31/502; C07D 401/06; C07D 405/14; C07D 417/14
(52) U.S. Cl. ........................ 514/248; 544/237
(58) Field of Search ........................ 544/237; 514/248

(56) References Cited

FOREIGN PATENT DOCUMENTS

| FR | 2 468 593 | 5/1981 |
| WO | WO 98/27066 | 6/1998 |
| WO | WO 99/32456 | 7/1999 |

OTHER PUBLICATIONS

Tetsutaro Ikeda, et al., Chemical Abstracts, vol. 55, No. 10, p. 11426, "Phthalazine and Related Compounds. VI.", 1961.
Tetsutaro Ikeda, et al., Chemical Abstracts, vol. 53, No. 4, p. 4288, "Phthalazine and Related Compounds. IV.", Feb. 25, 1959.

U.S. application No. 09/581,506, filed Aug. 10, 2000, pending.

U.S. application No. 09/581,505, filed Jul. 13, 2000, pending.

U.S. application No. 09/743,813, filed Jan. 22, 2001, pending.

U.S. application No. 09/806,496, filed Apr. 13, 2001, pending.

U.S. application No. 09/830,679, filed Apr. 30, 2001, pending.

U.S. application No. 09/764,983, filed Jan. 22, 2001, pending.

*Primary Examiner*—Emily Bernhardt
(74) *Attorney, Agent, or Firm*—Oblon, Spivak, McClelland, Maier & Neustadt, P.C.

(57) ABSTRACT

The present invention provides a compound selected from the group including: N-3-acetyl-1-(3,5-dichloropyridin-4-ylmethyl)-5-cyclopentyloxy-6-methoxy-4H-phthalazine; 6,7-dimethoxy-1-pyridin-4-ylmethyl-4-thiazol-2-yl-phthalazine; 1-(6,7-dimethoxy-4-pyridin-4-ylmethyl-1H-phthalazin-2-yl)ethanone; 2-methanesulphonyl-6,7-dimethoxy-4-pyridin-4-ylmethyl-1,2-dihydrophthalazine; 2-formyl-6,7-dimethoxy-4-pyridin-4-ylmethyl-1,2-dihydrophthalazine; 1-(6,7-dimethoxy-4-pyridin-4-ylmethyl-1H-phthalazin-2-yl)-1-imidazol-1-ylmethanone; 1-(3,5-dichloro-pyridin-4-ylmethyl)-3-methansulphonyl-6-difluoromethoxy-5-(tetrahydro-furan-2-yloxy)-4H-phthalazine; N→O derivatives thereof; and pharmaceutically acceptable salts thereof. The invention also provides a pharmaceutical composition, which contains a therapeutically effective amount of the above compound in admixture with a pharmaceutically acceptable carrier.

9 Claims, No Drawings

PHTHALAZINE DERIVATIVES AS PHOSPHODIESTERASE 4 INHIBITORS

This application is a 371 of PCT/EP99/05068 filed Jul. 16, 1999.

The present invention relates to phthalazine derivatives, to the pharmaceutical compositions containing them and to their use as phosphodiesterase 4 inhibitors. Phosphodiesterases are a family of isoenzymes which constitute the basis of the main mechanism of cAMP (cyclic adenosine-3',5'-monophosphate) hydrolytic inactivation. cAMP has been shown to be the second messenger mediating the biologic response to many hormones, neurotransmitters and drugs [Krebs Endocrinology Proceedings of the 4th International Congress Excerpta Medica, 17–29, 1973]. When the suitable agonist binds to the cell surface, the adenylated cyclase activates and turns $Mg^{2+}$-ATP into cAMP. cAMP modulates the activity of the majority, if not of all the cells contributing to the pathophysiology of various respiratory diseases, both of allergic origin and not. It follows that an increase of the cAMP concentration yields beneficial effects such as airway smooth muscle relaxation, inhibition of the mast cell mediator release (basophil granulose cells), suppression of the neutrophil and basophil degranulation, inhibition of the monocyte and macrophage activation. Thus, compounds able of activating adenylate cyclase or of inhibiting phosphodiesterases could suppress the undesired activation of the airway smooth muscle and of a great number of inflammatory cells.

In the phosphodiesterase family there is a distinct group of isoenzymes, phosphodiesterases 4 (hereinafter PDE 4) specific for the cAMP hydrolysis in the airway smooth muscle and inflammatory cells (Torphy, "Phosphodiesterase Isoenzymes: Potential Targets for Novel Anti-asthmatic Agents" in New Drugs for Asthma, Barnes, ed. IBC Technical Services Ltd, 1989). Studies carried out on this enzyme show that its inhibition yields not only the airway smooth muscle relaxation, but also the suppression of mastocyte, basophil and neutrophil degranulation, so as the inhibition of the monocyte and neutrophil activation. Thus PDE 4 inhibitors are effective in the therapy of asthma. Such compounds offer a unique approach to the therapy of various respiratory diseases, both of allergic origin and not, and possess significant therapeutic advantages over the current therapy.

The excessive or irregular production of tumour necrosis factor (hereinafter $TNF_\alpha$) a cytokine with pro-inflammatory activity produced by various kinds of cells, affects the mediation or the exacerbation of many pathologies such as, for example, the adult respiratory distress syndrome (ARDS) and the chronic pulmonary inflammatory disease. Therefore compounds able to control the negative effects of $TNF_\alpha$, i.e. the inhibitors of this cytokine, are to be considered as useful against many pathologies. The patent application EP-0 017 411 (in the name of Pfizer) illustrates phthalazines of formula:

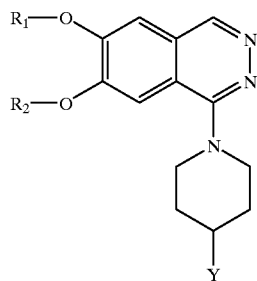

wherein
$R_1$ is a lower alkyl; and Y is —$(CH_2)_m$—Z wherein m is 1 or 2 and Z is carbamoyloxy, carbonylamino, sulphamoyl, ureido, amino-sulphamoyl, carboxyamino substituted in the terminal position by a $(C_{3-7})$ cycloalkyl. These compounds are said to be inhibitors of the phosphodiesterases with stimulant function on the cardiac muscle, therefore their activity does not relate to PDE 4.

The patent application EP-0 722 936 (in the name of Eisai) claims, inter alia, compounds of formula:

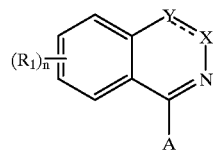

wherein n=0–4; $R_1$ is optionally substituted lower alkoxy, optionally substituted cycloalkyl, or a —$OR_9$ group wherein $R_9$ represents an optionally substituted arylalkyl group; X is —N═ or —$NR_6$— wherein $R_6$ is hydrogen, a lower alkyl group, or optionally substituted arylalkyl or heteroarylalkyl groups; Y is —CO or —CB═ wherein B is —$NR_7R_8$ wherein one of $R_7$ and $R_8$ may be H and the other an optionally substituted heteroarylalkyl group, or B is hydrogen or an optionally substituted aryl, heteroaryl, arylalkyl or heteroarylalkyl group; A is a hydrogen or halogen atom, or an optionally substituted mono or disubstituted amino group, an optionally substituted aryl, heteroaryl or heteroarylalkyl group. Among the groups optionally substituting the above mentioned residues halogen atoms are cited. These compounds are said to be active as inhibitors of cGMP-PDE, i.e. PDE 5, a phosphodiesterase just acting through a cGMP-dependent mechanism and whose field of application is markedly cardiovascular (Schudt C. et al., Phosphodiesterase Inhibitors, Academic Press). The patent U.S. Pat. No. 3,274,185 (in the name of Messengill) describes, inter alia, phthalazines of formula:

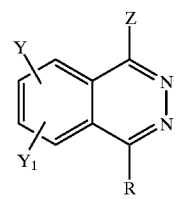

wherein Y and $Y_1$ are lower alkoxy; Z is phenyl optionally substituted by halogen or benzyl; and R is hydrogen. These phthalazines are endowed with sedative and hypotensive activity, with no mention of the mechanism of action.

The patent U.S. Pat. No. 3,813,384 (in the name of Asta-Werke) illustrates, inter alia, benzylphthalazinones of formula:

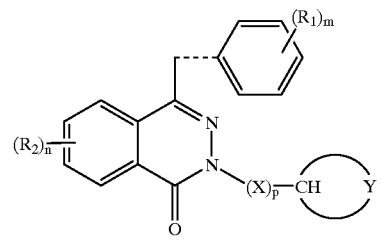

wherein $R_1$ and $R_2$ are lower alkoxy or halogen; X is an optionally branched alkylene chain; m and n are 1–3; p is 0 or 1; and

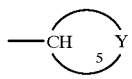

the group is a $C_{3-8}$ mono-, di- or tricyclic residue containing one or two nitrogen atom(s). Such compounds have hystaminolytic action and are useful, for example, in the treatment of asthma.

The patent application NL 8005411 (in the name of Mitsubishi Yuka) describes phthalazines of formula:

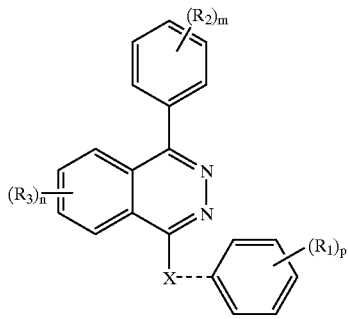

wherein X is oxygen or NH; $R_1$, $R_2$ and $R_3$ are, inter alia, $(C_{1-5})$alkyl, $(C_{1-5})$alkoxy, halogen or $CF_3$, n, m and p are 0–3. These compounds are used as inhibitors of the piastrinic aggregation.

The patent application JP-56061365 (in the name of Showa Denko) describes phthalazinones of formula:

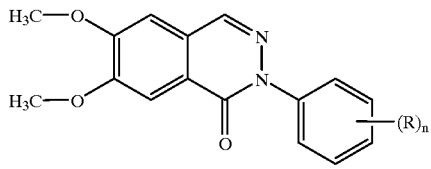

wherein, inter alia, R is halogen and n is 1–3, as vasodilators and anti-ulcer.

It has now been surprisingly found a new class of phthalazine derivatives able to inhibit PDE 4 and $TNF_\alpha$.

Therefore the present invention relates to compounds of formula I

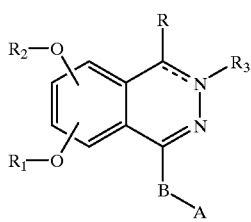

wherein
 === is a single or double bond;
 B is NH, methylene, a $C_{2-6}$ alkylene chain optionally branched and/or unsaturated and/or interrupted by a $C_{5-7}$ cycloalkyl residue;

A is phenyl or heterocycle optionally substituted by one or more substituent(s) or a $COR_4$ group wherein $R_4$ is hydroxy, $C_{1-4}$alkyl, amino optionally mono- or di-substituted by a $C_{1-6}$-alkyl group or monohydroxylated;

R represents two hydrogen atoms or a C=O group when === is a single bond or, when === is a double bond, is hydrogen, optionally substituted aryl or heterocycle, $(C_{1-8})$-alkyl, $(C_{2-8})$-alkenyl or $(C_{2-8})$-alkynyl optionally substituted by aryl or heterocycle; aryloxy, heterocyclyloxy, aryl-$C_{1-4}$-alkoxy, heterocyclyl-$C_{1-4}$-alkoxy, amino substituted by one or two $C_{1-4}$-alkyl group(s), aryl-amino, heterocyclyl-amino, aryl-$C_{1-4}$-alkyl-amino, heterocyclyl-$C_{1-4}$-alkylamino;

$R_1$ is a $C_{1-6}$-alkyl, aryl, aryl-$C_{1-10}$-alkyl, $C_{4-7}$-cycloalkyl group optionally containing an oxygen atom and/or substituted by a polar substituent;

$R_2$ is a $C_{1-6}$-alkyl, polyfluoro$C_{1-6}$-alkyl group;

$R_3$ is absent when === is a double bond, or, when === is a single bond, is hydrogen;

$C_{1-6}$-alkyl optionally substituted by aryl, by heterocycle or by a $COR_5$ group wherein $R_5$ is hydroxy, $C_{1-4}$-alkoxy or hydroxyamino;

—$COR_6$ wherein $R_6$ is hydrogen, aryl, aryl-$C_{1-6}$-alkyl, amino optionally alkylated or monohydroxylated, hydroxy, $C_{1-4}$-alkoxy, carboxy, $C_{1-4}$-alkoxycarbonyl,

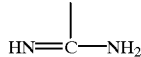

or $C_{1-4}$-alkyl optionally substituted by heterocycle;
d) $C_{1-4}$-alkyl-sulfonyl;
the N→O derivatives of the compounds of formula I and the pharmaceutically acceptable salts thereof;
provided that when === is a double bond, A is phenyl or nitrogen heterocycle, and $R_1$ is an aryl, aryl-$C_{1-10}$-alkyl, $C_{4-7}$-cycloalkyl optionally containing an oxygen atom and/or substituted by a polar substituent; then R is different from hydrogen, phenyl or $(C_{1-4})$alkyl optionally substituted by aryl.

The proviso present in the meanings of formula I has the aim of excluding the compounds described in the Italian patent application no. MI97A002806 in the name of the same Applicant.

Preferred compounds of formula I are those wherein === is a single or double bond;
B is methylene or a $C_{2-6}$ alkylene chain; A is phenyl or heterocycle optionally substituted by one or more substituents; R represents two hydrogen atoms or a group =O when === is a single bond, or, when === is a double bond, is hydrogen, optionally substituted aryl or heterocycle, $(C_{1-8})$-alkyl, $(C_{2-8})$-alkenyl or $(C_{2-8})$-alkynyl optionally substituted by aryl or heterocycle; aryloxy, heterocyclyloxy, aryl-$C_{1-4}$-alkoxy, heterocyclyl-$C_{1-4}$-alkoxy, amino substituted by one or two $C_{1-4}$-alkyl, aryl-amino, heterocyclyl-amino, aryl-$C_{1-4}$-alkyl-amino, heterocyclyl-$C_{1-4}$-alkylamino groups; $R_1$ is a $C_{1-6}$-alkyl, aryl, aryl-$C_{1-10}$-alkyl, $C_{4-7}$-cycloalkyl group optionally containing an oxygen atom and/or substituted by a polar substituent; $R_2$ is a $C_{1-6}$-alkyl, polyfluoro$C_{1-6}$-alkyl group; $R_3$ is absent when === is a double bond, or, when === is a single bond, is hydrogen;

$C_{1-6}$-alkyl optionally substituted by aryl, by heterocycle or by a $COR_5$ group wherein $R_5$ is hydroxy, $C_{1-4}$-alkoxy or hydroxyamino;

—COR$_6$ wherein R$_6$ is hydrogen, aryl, aryl-C$_{1-6}$-alkyl, optionally alkylated or monohydroxylated amino, hydroxy, C$_{1-4}$alkoxy, carboxy, C$_{1-4}$-alkoxycarbonyl, or C$_{1-4}$-alkyl optionally substituted by heterocycle;

C$_{1-4}$-alkyl-sulfonyl;

the N→O derivatives of the compounds of formula I and the pharmaceutically acceptable salts thereof;

provided that when === is a double bond, A is phenyl or nitrogen heterocycle, and R$_1$ is an aryl, aryl-C$_{1-10}$-alkyl, C$_{4-7}$-cycloalkyl group optionally containing an oxygen atom and/or substituted by a polar substituent; then R is different from hydrogen, phenyl or (C$_{1-4}$)alkyl optionally substituted by aryl.

Still more preferred compounds of formula I are those wherein === is a double bond;

B is methylene; A is pyridine substituted by one or more substituents; R is optionally substituted aryl or heterocycle, (C$_{1-8}$)-alkyl, (C$_{2-8}$)-alkenyl or (C$_{2-8}$)-alkynyl optionally substituted by aryl or heterocycle, aryloxy, heterocyclyloxy, aryl-C$_{1-4}$-alkoxy, heterocyclyl-C$_{1-4}$-alkoxy, amino substituted by one or two C$_{1-4}$-alkyl, aryl-amino, heterocyclyl-amino, aryl-C$_{1-4}$-alkyl-amino, heterocyclyl-C$_{1-4}$-alkylamino groups; R$_1$ is a C$_{1-6}$-alkyl or C$_{4-7}$-cycloalkyl group optionally containing an oxygen atom and/or substituted by a polar substituent; R$_2$ is a C$_{1-6}$-alkyl, polyfluoroC$_1$-alkyl group; R$_3$ is absent; the N→O derivatives of the compounds of formula I and the pharmaceutically acceptable salts thereof.

The compounds of formula I may have one or more asymmetric centre(s) and thus be in the form of stereoisomers. Object of the present invention are compounds of formula I in the form of stereoisomeric mixtures so as of single stereoisomers.

The compounds of formula I are active as PDE 4 and TNF$_\alpha$ inhibitors and thus are used as therapeutic agents in allergic and inflammatory pathologies such as, for example, emphysema, chronic bronchitis, asthma and allergic rhinitis.

As heterocycle pyrrole, imidazole, pyrazole, pyridine, pyrazine, pyrimidine, pyridazine, piperazine, triazine, morpholine, pyrrolidine, pyrroline, imidazoline, pyrazoline, pyrazolidine, imidazolidine, piperidine, fuiran, pyran, isothiazole, isoxazole, thiophene and the like are particularly meant. The substituents optionally present on A residues may be halogen, which means a fluorine, chlorine, bromine or iodine atom, oxo, nitro, carboxy, trifluoromethyl, amino.

Specific example of alkyl groups are methyl, ethyl, n-propyl, i-propyl, n-butyl, s-butyl, t-butyl, 2-methyl-propyl, n-pentyl, 1-methyl-butyl, 2-methyl-butyl, 3-methyl-butyl, 3-methyl-2-butyl, n-hexyl and the like. As (C$_{5-7}$) cycloalkyl group cyclopentyl, cyclohexyl and cycloheptyl are meant, and when it is substituted by an oxygen atom, tetrahydrofuran or tetrahydropyran, for example, are meant, while aryl and aryl-C$_{1-10}$-alkyl mean an aromatic ring or a system of 6–10 carbon atoms such as, for example, phenyl, benzyl, phenethyl, phenyl-pentyl, naphthyl, indanyl, indanyl-pentyl and the like.

The oxidised form N→O, if present, may involve both the nitrogen atoms of the phthalazine ring and those present on A when it is a heterocyclic substituent.

Pharmaceutically acceptable salts of the compounds of formula I are those with organic and inorganic acids, such as, for example, hydrochloric, hydrobromic, hydroiodic, nitric, sulfuric, phosphoric, acetic, benzoic, maleic, fumaric, tartaric, citric, aspartic, succinic, methanesulfonic, 3,7-di-t.butylnaphthalen-1,5-disulfonic (dibudinic acid) or with inorganic bases such as, for example, sodium or potassium hydroxide, sodium bicarbonate.

The synthesis of the compounds of formula I proceeds according to methods known to the skilled in the art. For example, an acid of formula II;

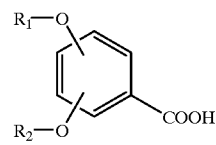

(II)

wherein R$_1$ and R$_2$ are as defined above, which, for example by treatment with a halogenating agent, for example thionyl chloride, is transformed into the corresponding acyl halide of formula III:

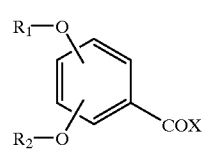

(III)

wherein R$_1$ and R$_2$ are as defined above and X is chlorine or bromine. This compound is reacted with diethylamine in at least equimolar amounts, to give a benzamide of formula IV:

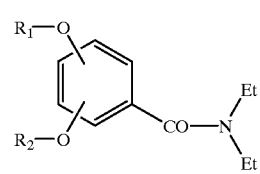

(IV)

wherein R$_1$ and R$_2$ are as defined above, which, with dimethylformamide in the presence of a strong organic base such as, for example, butyl-lithium, t-butyl-lithium, sec-butyl-lithium, and, optionally, of a ligand such as, for example tetramethylethylendiamine, gives a compound of formula Va:

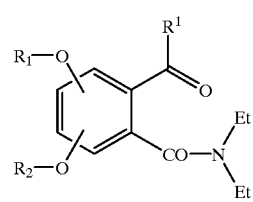

(Va)

wherein R$_1$ and R$_2$ are as defined above, and R$^I$ is hydrogen.

When a compound of formula I wherein R is hydrogen is desired, the compound Va is reacted with an equimolar amount of ter-butylcarbazate to give the compound of formula VIa:

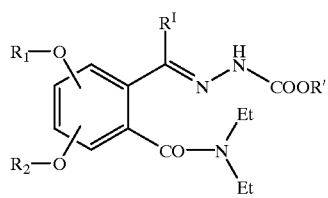

(VIa)

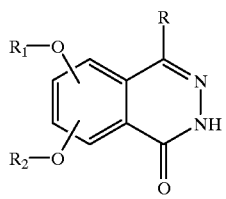

(VIII)

wherein $R^I$, $R_1$ and $R_2$ are as defined above, and R' is a protecting group of the carboxylic function such as, for example, t-butyl.

When a compound of formula I wherein R is different from hydrogen and ═══ is a double bond is desired, the compound IV is treated with $R^{II}$-magnesium halide, for example chloride, or $R^{II}$-lithium, wherein $R^{II}$ is aryl, arylalkyl, arylalkenyl, arylalkynyl, heterocycle, heterocyclylalkyl, heterocyclylalkenyl, heterocyclylalkynyl, $C_{1-8}$-alkyl, $C_{2-8}$-alkenyl or $C_{2-8}$-alkynyl, linear or branched, optionally interrupted by an heteroatom selected among oxygen and nitrogen and optionally substituted by a suitably protected hydroxy or oxo group, to give a compound of formula VII:

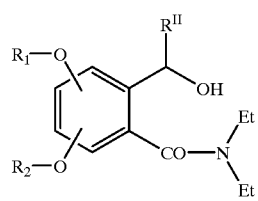

(VII)

wherein $R^{II}$, $R_1$ and $R_2$ are as defined above. The compound VII is treated with a suitable oxidising agent such as, for example, pyridinium-chloro-chromate, and gives a compound of formula Vb:

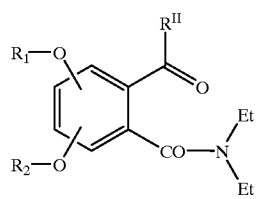

(Vb)

wherein $R_1$, $R_2$ and $R^{II}$ are as defined above, which treated with an equimolar amount of ter-butylcarbazate gives the compound of formula VIb:

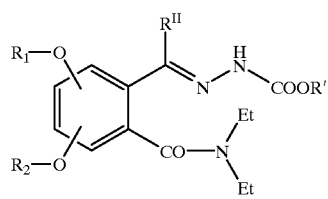

(VIb)

wherein $R_1$, $R_2$, R' and $R^{II}$ are as defined above.

The compound VIa or VIb is reacted with trifluoroacetic acid to give the phthalazinone of formula VIII:

wherein R, $R_1$ and $R_2$ are as defined above. This phthalazinone is reacted with a halogenating agent such as, for example, phosphoryl chloride, to give the phthalazine of formula IX:

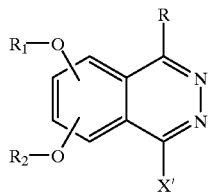

(IX)

wherein R, $R_1$ and $R_2$ are as defined above, and X' is a halogen atom.

Alternatively, the compound of formula VIII can be obtained directly from the compound of formula Va or Vb by treatment with hydrazine in acetic acid.

The compound IX gives a compound I by reaction with a compound of formula X $$A-B'-Y \quad \quad (X)$$

wherein A is as defined above, B' is methylene, ethylene or amino and Y is a metal such as, for example, Li, Na, Mg or a transition metal complex, gives a compound I wherein R has the above reported meanings when ═══ is a double bond.

Alternatively, the compounds I wherein B is different from amino can be obtained starting from the acid of formula 11, which by reaction with formaldehyde/HCl gives a compound of formula XI:

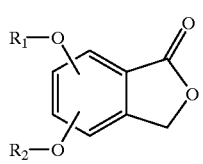

(XI)

wherein $R_1$ and $R_2$ are as defined above. This compound is oxidised, for example with benzoyl peroxide/N-bromosuccinimide, and then hydrolysed to give a compound of formula XII:

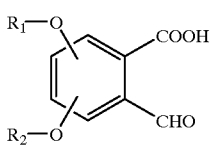

(XII)

wherein $R_1$ and $R_2$ are as defined above, which with a halogenidric acid and triphenylphosphine gives a compound of formula XIII:

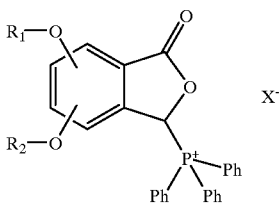

(XIII)

wherein $R_1$ and $R_2$ are as defined above, which treated with an aldehyde of formula XIV:

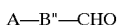

A—B"—CHO (XIV)

wherein A is as defined above and B" is methylene or a $C_{2-5}$ alkylene chain optionally branched and/or unsaturated and/or interrupted by a $C_{5-7}$ cycloalkyl residue, or is absent, in the presence of an organic base such as, for example triethylamine, gives a compound of formula XV:

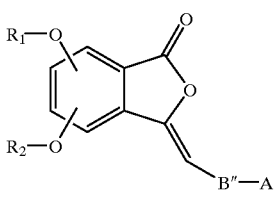

(XV)

wherein $R_1$, $R_2$, B" and A are as defined above. This is reacted with hydrazine to give a compound of formula XVI:

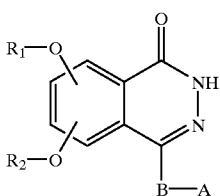

(XVI)

wherein $R_1$, $R_2$, and A are as defined above and B is different from amino, which is treated with a halogenating agent, such as phosphoryl chloride or bromide, to give a compound of formula XVII:

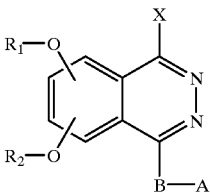

(XVII)

wherein $R_1$, $R_2$, X and A are as defined above and B is different from amino. This compound subdue to a coupling reaction with the suitable metallo-organic derivative in the presence of a catalyst, for example, a palladium catalyst, or to a nucleophilic substitution gives a compound of formula I wherein === is a double bond and B is different from amino.

The compound of formula XVI reacted with a suitable alkyl halide or sulphonate in the presence of a base, for example, sodium hydride, gives a compound of formula I wherein $R_3$ is a substituent different from hydrogen and R is =O.

Alternatively, the compound of formula XVII can be hydrogenated, for example with Pd/C in the presence of a base, to a compound of formula XVIII:

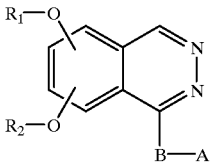

(XVIII)

wherein $R_1$, $R_2$, and A are as defined above and B is different from amino, which by further hydrogenation, for example with $PtO_2$, gives the compound of formula XIX:

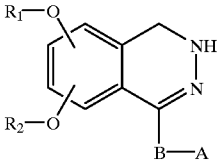

(XIX)

wherein $R_1$, $R_2$, B and A are as defined above, which by subsequent treatment with the suitable acylating or sulphonating agent, gives a compound of formula I wherein === is a single bond and $R_3$ is different from hydrogen.

The synthesis of the N-oxides of the compounds of formula I occurs by treating the compounds of formula I with peracids such as, for example, m-chloroperbenzoic acid.

The preparation of the salts of the compounds I is effected according to conventional methods.

The compounds of formula I are PDE 4 inhibitors as showed by the in vitro enzymatic inhibition activity tests (example 41), and also are able to inhibit the $TNF_\alpha$ release. Comparisons with the following compounds were made: 6,7-dimethoxy-4-(pyridin-4-yl-methyl)-2H-phthalazin-1-one (reference 1) and 6,7-dimethoxy-4-(piperidin-4-yl-methyl)-2H-phthalazin-1-one (reference 2) comprised by the general formula of the patent application EP-0 722 936 (in the name of Eisai) already cited above, selected in view of their structural affinity with the compounds of the invention. The reference compounds, though chemically similar, showed to be inactive as PDE 4 inhibitors.

It is apparent how these selectivity and specificity features combined with the lack of activity on the cardiovascular system make the compounds of formula I specifically suitable for treating pathologies involving PDE 4 and $TNF_\alpha$ such as asthma, the chronic obstructive pulmonary disease (COPD), the adult respiratory distress syndrome (ARDS), allergic rhinoconjunctivitis, psoriasis, atopic dermatitis, rheumatoid arthritis, septic shock, ulcerative cholitis, even if in the present contest the interest is particularly focused on the respiratory pathologies. Especially, the compounds of the invention are useful in the treatment of allergic and inflammatory diseases and above all in the therapy of COPD, asthma and allergic rhinitis.

The therapeutic doses shall be generally comprised between 0.1 and 1,000 mg a day and between 1 and 100 mg by oral route for single administration.

A further object of the present invention are the pharmaceutical compositions containing a therapeutically effective amount of the compounds of formula I or pharmaceutically acceptable salts thereof in admixture with a suitable carrier.

The pharmaceutical compositions object of the invention can be liquid, suitable for the enteral or parenteral administration, and, preferably, solid such as tablets, capsules, granulates, suitable for the oral administration, or in a form suitable for the transdermal and inhalatory administration.

The preparation of the pharmaceutical compositions object of the invention can be effected according to common techniques.

For better illustrating the invention the following examples are provided.

EXAMPLE 1

Synthesis of 3-cyclopentyloxy-4-methoxy benzoic acid

A solution of tetrabutylammonium bromide (111.68 g, 0.336 moles) in water (400 ml) was added under stirring to a solution of potassium permanganate (53.1 g, 0.336 moles) in water (1 l). The obtained solid was separated by filtration, washed with water and dissolved in 500 ml of pyridine. This solution was dropped into one of crude 3-cyclopentyloxy-4-methoxy benzaldehyde (obtained as described in J. Med. Chem., 1995, 38, page 4851) (74 g, 0.336 moles) in pyridine (200 ml), under stirring in water/ice. At the end 3 l of ice were added and it was acidified by dropping 850 ml of 12N HCl. The stirring was kept for further 1.5 hours, then the solid was separated by filtration and extracted under stirring for 30 minutes with ethyl acetate (2 l). The residual solid was removed and the mother liquors were further extracted with ethyl acetate (2×700 ml). The organic phases were washed with water, dried on sodium sulphate and concentrated to small volume to give 53.2 g of the title compound (yield: 67%).

$^1$H-NMR (200 MHz, $CDCl_3$) δ (ppm): 7.75–6.87 (m, 3H); 4.87–4.79 (m, 1H); 3.90 (s, 3H); 2.08–1.52 (m, 8H).

EXAMPLE 2

Synthesis of 3-cyclopentyloxy-4-methoxy benzoyl chloride

A solution of 3-cyclopentyloxy-4-methoxy benzoic acid (53 g, 0.224 moles), obtained as described in example 1, in thionyl chloride (200 ml) was put under reflux for 2 hours under nitrogen, evaporated to dryness and taken up twice with toluene (100 ml) to give 57 g of the title compound which was used as such in the subsequent step.

$^1$H-NMR (200 MHz, $CDCl_3$) δ (ppm): 7.81–7.72 (dd, 1H); 7.52–7.50 (d, 1H); 6.91–6.85 (d, 1H); 4.87–4.75 (m, 1H); 3.91 (s, 3H); 2.08–1.50 (m, 8H).

EXAMPLE 3

Synthesis of 3-cyclopentyloxy-N,N-diethyl-4-methoxy-benzamide

Diethylamine (69.2 g, 0.672 moles) was added dropwise at 5–10° C. to a solution of 3-cyclopentyloxy-4-methoxy benzoyl chloride (57 g, 0.224 moles) obtained as described in example 2, in methylene chloride (250 ml). The mixture was evaporated to dryness, dissolved in ethyl acetate, washed with water, with 2% potassium bisulphate, again with water and sodium bicarbonate, dried on sodium sulphate and brought to dryness. The residue was taken up with petrolatum (250 ml) to give 61.2 g of the title compound (yield: 94%).

$^1$H-NMR (200 MHz, $CDCl_3$) δ (ppm): 6.94–6.78 (m, 3H); 4.80–4.70 (m, 1H); 3.82 (s, 3H); 3.50–3.22 (m, 4H); 1.98–1.50 (m, 8H) 1.17 (broad t, 6H).

EXAMPLE 4

Synthesis of 3-cyclopentyloxy-N,N-diethyl-2-formyl-4-methoxy-benzamide

At −75° C. under stirring, sec-butyl-lithium (195.76 ml, 0.231 moles) and, after 1 hour, at the same temperature, dimethylformamide (53.66 ml, 0.693 moles) were added dropwise to a solution of 3-cyclopentyloxy-N,N-diethyl-4-methoxy-benzamide (61.2 g, 0.21 moles), obtained as described in example 3, and of tetramethylendiamine (34.86 ml, 0.231 moles) in anhydrous tetrahydrofuran (480 ml). After further half an hour at −75° C., the reaction mixture was poured into a pH=7 phosphate buffer, ethyl acetate and concentrated HCl. The extraction was repeated further twice with fresh ethyl acetate, then the extract was washed with 5% potassium bisulphate, then with water, then dried on sodium sulphate and evaporated to dryness. The residue was cromatographed on silica gel (eluent petrolatum/ethyl acetate 1:1) to give 23.3 g of the title compound (yield: 35%).

$^1$H-NMR (200 MHz, $CDCl_3$) δ (ppm): 10.44 (s, 1H); 7.09–6.85 (m, 2H); 5.05–4.98 (m, 1H); 3.84 (s, 3H); 3.59–3.47 and 3.05–2.92 (2q, 4H); 1.95–1.52 (m, 8H), 0.95 (2t, 6H).

EXAMPLE 5

Synthesis of N'-(2-cyclopentyloxy-6-diethylcarbamoyl-3-methoxy-benzylidene)-hydrazincarboxylic acid ter-butyl ester A solution of 3-cyclopentyloxy-N,N-diethyl-2-formyl-4-methoxy-benzamide (21.7 g, 0.068 moles) obtained as described in example 4, and ter-butylcarbazole (112.84 g, 0.1 moles) in absolute ethanol (217 ml) was kept under reflux for 3 hours, brought to dryness, taken up with petrolatum and brought again to dryness. The residue was taken up with ethyl ether (100 ml) and petrolatum (200 ml), filtered and the mother liquors were brought to dryness to give 27.45 g of the title compound (yield: 93%).

$^1$H-NMR (200 MHz, $CDCl_3$) δ (ppm): 8.60 (m, 1H); 8.05 (broad-s, 1H); 6.87 (s, 2H); 4.87–4.72 (m, 1H); 3.82 (s, 3H);

3.58–3.25 (m, 4H); 1.90–1.50 (m, 8H); 1.40 (s, 9H); 1.22–1.06 (2t, 6H).

EXAMPLE 6

Synthesis of 5-cyclopentyloxy-6-methoxy-2H-phthalazin-1-one

N'-(2-cyclopentyloxy-6-diethylcarbamoyl-3-methoxy-benzylidene)-hydrazincarboxylic acid ter-butyl ester (27.35 g, 0.063 moles) obtained as described in example 5, was added to 150 ml of trifluoroacetic acid, under stirring at 5–10° C., the mixture was kept under stirring for 15 minutes and brought to dryness. The residue was dissolved in methylene chloride (750 ml) and kept at room temperature for 6 hours, then washed with 5% $Na_2CO_3$ up to alkalinity, then with water, then dried on sodium sulphate and evaporated to dryness. The residue was taken up with 100 ml of ethyl ether and filtered to give 15.58 g of the title compound (yield: 95%).

$^1$H-NMR (200 MHz, $CDCl_3$) δ (ppm): 10.12 (m, 1H); 8.84 (s, 2H); 8.11 and 7.36 (2d, 2H); 5.11–5.01 (m, 1H); 3.98 (s, 3H); 2.00–1.60 (m, 8H).

EXAMPLE 7

Synthesis of 1-chloro-5-cyclopentyloxy-6-methoxy-2H-phthalazine

A suspension under nitrogen of 5-cyclopentyloxy-6-methoxy-2H-phthalazin-1-one (7.5 g, 28.81 mmoles), obtained as described in example 6, in $POCl_3$ (30 ml) was kept under stirring at 80° C., then concentrated to dryness, the residue was dissolved in ethyl acetate and washed with $K_2CO_3$ up to alkalinity, then with water, dried on $Na_2SO_4$ and evaporated to dryness yielding 7.95 g of the title compound (yield: 99%).

$^1$H-NMR (200 MHz, $CDCl_3$) δ (ppm): 8.40 (s, 2H); 8.11 and 7.36 (2d, 2H); 5.11–5.01 (m, 1H); 3.98 (s, 3H); 2.00–1.60 (m, 8H).

EXAMPLE 8

Synthesis of 1-(3,5-dichloropyridin-4-yl-methyl)-5-cyclopentyloxy-6-methoxy-phthalazine Under stirring, 55% sodium hydride (3.73 g, 85.56 mmoles) was added to a solution, under nitrogen, of 3,5-dichloro-4-methyl-pyridine (13.86 g, 85.56 mmoles) in anhydrous DMF (100 ml). The mixture was kept under stirring for 1 hour then added with a solution of 1-chloro-5-cyclopentyloxy-6-methoxy-phthalazine (7.95 g, 28.52 mmoles), obtained as described in example 7, in anhydrous dimethylformamide (70 ml). After resting overnight, the mixture was quenched with water, diluted with water and extracted with ethyl acetate. The extract was washed with water and dried on sodium sulphate, then evaporated to dryness. The residue was flash chromatographed (eluent petrolatum/ethyl acetate 1:1) to give 6.58 g of the title compound (yield: 57%).

$^1$H-NMR (200 MHz, $CDCl_3$) δ (ppm): 8.92 (s, 1H); 8.49 (s, 2H); 7.89 (d, 1H, JHH=9.1 Hz); 7.63 (d, 1H); 5.21–5.14 (m, 1H); 4.86 (s, 2H); 4.03 (s, 3H); 1.98–1.57 (m, 8H).

EXAMPLE 9

Synthesis of N-3-acetyl-1-(3,5-dichloropyridin-4-ylmethyl)-5-cyclopentyloxy-6-methoxy-4H-phthalazine (Compound 1)

A solution of 1-(3,5-dichloropyridin-4-ylmethyl)-5-cyclopentyloxy-6-methoxy-phthalazine (1 g, 2.47 mmoles), obtained as described in example 8, in glacial acetic acid (35 ml) and 10% Pd/C in catalytic amount, under nitrogen at room temperature, was charged into a Parr hydrogenator at 4.08 bar. After 3 days the solution was filtered on celite and the mother liquors brought to dryness. The residue was flash chromatographed (eluent: hexane/ethyl acetate 6:4, then 3:7) to give 0.12 g of the title compound (yield: 10.9%). m.p.: 128–130° C.

$^1$H-NMR (200 MHz, $CDCl_3$) δ (ppm): 8.46 (s, 2H); 7.21 (d, 1H, JHH=8.2Hz); 6.86 (d, 1H); 4.96–4.86 (m, 1H); 4.81 (s, 2H); 4.26 (s, 2H); 3.87 (s, 3H); 1.81 (s, 3H); 1.48 (m, 8H).

EXAMPLE 10

Synthesis of 5,6-dimethoxy-3H-isobenzofuran-1-one

A suspension of 3,4-dimethoxy-benzoic acid (353.5 g, 1.94 moles) in HCHO (1.7 l, 24.5 moles) under stirring was prepared and cooled in ice, saturated with gaseous HCl (340 g, 9.32 moles), then gradually warmed to 60° C. After one night the temperature was cooled to the room value and further HCl (300 g) was bubbled in, then the temperature was brought again to 60° C. for one night. The mixture was partially evaporated, taken up in water (1 l), neutralised with 28% $NH_4OH$ (1.5 l) and kept at cold for 2 hours, then filtered. The filtrate was washed with water up to neutrality, then crystallised from methanol (2 l) and dried under vacuum at 60° C. to give 220 g of the title compound (yield: 58.65%).

$^1$H-NMR (200 MHz, $CDCl_3$) δ (ppm): 7.28 and 6.28 (2s, 2H); 5.20 (s, 2H); 3.95 and 3.91 (2s, 6H).

EXAMPLE 11

Synthesis of 2-formyl-4,5-dimethoxy-benzoic acid

A mixture under nitrogen of 5,6-dimethoxy-3H-isobenzofuran-1-one (10 g, 51.5 mmoles), obtained as described in example 10, in carbon tetrachloride (250 ml), N-bromo-succinimide (13.88 g, 77.25 mmoles) and benzoyl peroxide (320 mg, 1.23 mmoles) was brought to reflux for 2 hours, then cooled, filtered and washed with a 10% $Na_2SO_3$ solution (200 ml), then with water, dried and brought to dryness. The residue was taken up in 5% HCl (100 ml) and kept under reflux for 4 hours, then the solution was cooled, basified with NaOH, washed with ethyl acetate and slowly acidified again to give a precipitate which was filtered and washed with water and dried on $P_2O_5$ under vacuum to give 6.43 g of the title compound (yield: 60%).

EXAMPLE 12

Synthesis of (5,6-dimethoxy-3-oxo-1,3-dihydro-isobenzofuran-1-yl)-triphenyl-phosphonium bromide A suspension under nitrogen of 2-formyl-4,5-dimethoxy-benzoic acid (6.43 g, 30.62 mmoles), obtained as described in example 11, triphenyl-phosphine (8.3 g, 30,62 mmoles), 30% HBr in acetic acid (8.26 ml, 30.62 mmoles) and glacial acetic acid (20 ml) was heated at 90° C. for 4.5 hours. The mixture was brought to dryness and dissolved again in acetonitrile (50 ml) and diluted with ethyl ether up to turbidity, then cooled and filtered, and the filtrate was washed with ethyl ether and dried under vacuum to give 13.6 g of the title compound (yield: 83%).

$^1$H-NMR (200 MHz, DMSO) δ (ppm): 8.35 and 7.31 (2s, 2H); 8.03–7.66 (m, 15H); 6.01 (s, 1H); 3.84 and 3.45 (2s, 6H).

EXAMPLE 13

Synthesis of 5,6-dimethoxy-3-pyridin-4-ylmethylene-3H-isobenzofuran-1-one

Triethylamine (20 ml, 145 mmoles) was added dropwise to a suspension of (5,6-dimethoxy-3-oxo-1,3-dihydro-isobenzofuran-1-yl)-triphenylphosphonium bromide (78 g, 145 mmoles), obtained as described in example 12, and 4-pyridincarboxaldehyde (13.0 ml, 145 mmoles) in methylene chloride (1 l), at room temperature, under stirring. After 1.5 hours the mixture was filtered and evaporated and the residue was treated with boiling ethanol, cooled and filtered. The mother liquors were chromatographed (eluent: methylene chloride then with 1% methanol) and the residue was brought to dryness and joined to the above filtrate to give 25 g of the title compound.

EXAMPLE 14

Synthesis of 6,7-dimethoxy-4-pyridin-4-ylmethyl-2H-phthalazin-1-one 5,6-Dimethoxy-3-pyridin-4-ylmethylene-3H-isobenzofuran-1-one (25 g, 88.34 mmoles), obtained as described in example 13, was reacted with hydrazine hydrate (500 ml) for 2 hours at room temperature under stirring, then for 1 hour at boiling. The mixture was diluted with water (300 ml), cooled and filtered to give 23 g of the title compound (yield: 87%).

EXAMPLE 15

Synthesis of 1-chloro-6,7-dimethoxy-4-pyridin-4-ylmethyl-phthalazine

A suspension of 6,7-dimethoxy-4-pyridin-4-ylmethyl-2H-phthalazin-1-one (10 g, 33.6 mmoles), obtained as described in example 14, in $POCl_3$ (70 ml) was heated at 90° C. for 4 hours. $POCl_3$ was evaporated and the residue dissolved in water, a saturated $NaHCO_3$ solution and NaOH up to obtaining a precipitate which was filtered and suspended in methanol, brought to dryness, suspended again in acetone and filtered again. The residue was dried at 45° C. under vacuum to give 9.562 g of the title compound.

EXAMPLE 16

Synthesis of 6,7-dimethoxy-1-pyridin-4-ylmethyl-4-thiazol-2-yl-phthalazine (Compound 2)

In anhydrous environment, bromothiazole (831 mg, 5.067 mmoles) and 2:1 THF/toluene (15 ml) were added dropwise to powder zinc (500 mg, 7.6 mmoles), with mild heating. The mixture was brought to reflux for 1.5 hours, then added with 1-chloro-6,7-dimethoxy-4-pyridin-4-ylmethyl-phthalazine (800 mg, 2.53 mmoles), obtained as described in example 15, palladium acetate (28 mg) and triphenylphosphine (66 mg). The mixture was kept under reflux for 3 hours, then added with palladium acetate (56 mg) and triphenylphosphine (133 mg) and kept under reflux overnight. Further palladium acetate (56 mg) and triphenylphosphine (133 mg) were added and after 4 hours the mixture was poured into methylene chloride/30% aqueous ammonia. The phases were separated and the organic one was washed with water, dried and brought to dryness to give a crude which was chromatographed (eluent: methylene chloride/methanol 2.4%) to give 354 mg of the title compound (yield: 38.4%).

$^1$H-NMR (200 MHz, $CDCl_3$) δ (ppm): 9.31 (s, 21H); 8.52–7.24 (m, 4H); 8.06 (d, 1H, JHH=3.4Hz); 7.52 (d, 1H); 7.11 (s, 1H); 4.69 (s, 2H); 4.11 and 3.92 (2s, 6H).

EXAMPLE 17

Synthesis of 6,7-dimethoxy-1-pyridin-4-ylmethyl-phthalazine

A solution of 1-chloro-6,7-dimethoxy-4-pyridin-4-ylmethyl-phthalazine (3 g, 9.5 mmoles), obtained as described in example 15, in DMF (50 ml), 32% NaOH (1.32 ml, 14.3 mmoles) and 10% Pd/C (0.69 g) was charged in a Parr reactor and hydrogenated at 2.38 bar for 2 hours. The catalyst was filtered off and the solution containing the title compound was used as such in the subsequent step.

EXAMPLE 18

Synthesis of 6,7-dimethoxy-1-pyridin-4-ylmethyl-3,4-dihydro-phthalazine

A solution of 6,7-dimethoxy-1-pyridin-4-ylmethyl-phthalazine (0.8 g, 28.44 mmoles), obtained as described in example 17, in methanol/THF 3:2 (25 ml) and $PtO_2$ (0.025 g) was charged in a Parr reactor under hydrogen at 4.08 bar. After one night the mixture was filtered over celite and brought to dryness to give a residue which was flash chromatographed (eluent: methylene chloride/methanol 97:3 than 95:5). There were obtained 0.15 g of the title compound.

$^1$H-NMR (200 MHz, $CDCl_3$) δ (ppm): 8.43–7.12 (m, 4H); 6.57 and 6.54 (2s, 2H); 4.07 (s, 2H); 4.00 (s, 2H); 3.80 and 3.65 (2s, 6H).

EXAMPLE 19

Synthesis of 1-(6,7-dimethoxy-4-pyridin-4-ylmethyl-1H-phthalazin-2-yl)ethanone (Compound 3)

A solution of 6,7-dimethoxy-1-pyridin-4-ylmethyl-3,4-dihydro-phthalazine (3.36 mmoles), obtained as described in example 18, in DMF (20 ml) was filtered on celite under nitrogen and the filtrate was dried under vacuum and washed with DMF (5 ml). Triethylamine (0.69 ml, 0.5 g, 4.9 mmoles) and, at 0° C., acetic anhydride (0.44 ml, 0.47 g, 4.65 mmoles) were added under nitrogen to this solution. The temperature was allowed to arise to the room value and after 1 hour acetic anhydride (0.06 ml, 0.67 mmoles) was added. After 30 minutes at room temperature and a week at 4° C., the mixture was concentrated to small volume, taken up with ethyl acetate, washed with a saturated solution of NaCl. The phases were separated and the organic one was dried and concentrated to give a residue, which was flash, chromatographed (eluent: methylene chloride/methanol 98:2). The resultant solid was triturated in ethyl acetate to give 0.582 g of the title compound (yield: 48%).

$^1$H-NMR (200 MHz, $CDCl_3$) δ (ppm): 8.53–7.21 (m, 4H); 6.71 and 6.63 (2s, 2H), 4.86 (s, 2H); 4.00 (s, 2H); 3.86 and 3.73 (2s, 6H); 2.26 (s, 3H).

EXAMPLE 20

Synthesis of 2-methanesulphonyl-6,7-dimethoxy-4-pyridin-4-ylmethyl-1,2-dihydro-phthalazine and 2-formyl-6,7-dimethoxy-4-pyridin-4-ylmethyl-1,2-dihydro-phthalazine (Compound 4 and 5)

By working analogously to what described in example 19, using 6,7-dimethoxy-1-pyridin-4-ylmethyl-3,4-dihydro-phthalazine (3.36 mmoles), obtained as described in example 18, in DMF (20 ml), triethylamine (0.69 ml, 0.5 g, 4.9 mmoles) and CH$_3$SO$_2$Cl (0.36 ml, 0.53 g, 4.65 mmoles), a mixture was obtained which was worked up as in example 19, but with CH$_2$Cl$_2$ instead of ethyl acetate. The residue was chromatographed (eluent: toluene/methanol from 95:5 to 87.5:12.5) to give, after treatment with isopropyl ether, 0.199 g of Compound 5 (first eluted) and 0.137 g of Compound 4 (yield: 19% and 11%).

Compound 4: $^1$H-NMR (200 MHz, CDCl$_3$) δ (ppm): 8.53–8.48 and 7.24–7.20 (2m, 4H); 6.71 and 6.67 (2s, 2H), 4.48 (s, 2H); 4.03 (s, 2H); 3.88 and 3.73 (2s, 6H); 3.07 (s, 3H).

Compound 5: $^1$H-NMR (200 MHz, CDCl$_3$) δ (ppm): 8.69 (s, 1H); 8.54–8.51 and 7.25–7.22 (2m, 4H); 6.69 and 6.63 (2s, 2H); 4.85 (s, 2H); 4.00 (s, 2H); 3.88 and 3.71 (2s, 6H).

EXAMPLE 21

Synthesis of 1-(6,7-dimethoxy-4-pyridin-4-ylmethyl-1H-phthalazin-2-yl)-1-imidazol-1-yl methanone (Compound 6)

To a solution under nitrogen of 6,7-dimethoxy-1-pyridin-4-ylmethyl-3,4-dihydro-phthalazine (2.81 mmoles), obtained as described in example 18, in DMF (16.5 ml), 1,1'-carbonyldiimidazole (0.75 g, 4.65 mmoles) was added. After 1 hour at room temperature and a week at 4° C., the mixture was concentrated, taken up with ethyl acetate, washed with a saturated solution of NaCl. The phases were separated and the organic one was dried and concentrated to give a residue, which was flash, chromatographed (eluent: methylene chloride/methanol 98:2). The resultant solid was triturated in isopropyl ether to give 0.135 g of the title compound (yield: 13%).

$^1$H-NMR (200 MHz, CDCl$_3$) δ (ppm): 8.56–7.19 (m, 4H); 8.30 (broad-s, 1H); 7.56 and 6.97 (2m, 2H); 6.80 and 6.71 (2s, 2H), 4.95 (s, 2H), 4.07 (s, 2H); 3.91 (2s, 6H).

EXAMPLE 22

Synthesis of 3-(4-hydroxy-benzyliden)-5,6-dimethoxy-3H-isobenzofuran-1-one

A solution of (5,6-dimethoxy-3-oxo-1,3-dihydro-isobenzofuran-1-yl)-triphenylphosphonium bromide (1 g, 1.87 mmoles), obtained as described in example 12, 4-hydroxy-benzaldeyde (230 mg, 1.87 mmoles) and triethylamine (263 μl) in CH$_2$Cl$_2$ (10 ml), was kept for 1 night at room temperature under nitrogen, washed with water, dried and brought to dryness. The residue was taken up with ethanol, kept under reflux for 3 hours, cooled, filtered and dried under vacuum to give 0.3 g of the title compound (yield: 54%).

$^1$H-NMR (200 MHz, DMSO) δ (ppm): 9.82 (s, 1H); 7.63–6.82 (m, 4H); 7.63, 7.32 and 6.72 (3s, 3H); 3.95 and 3.87 (2s, 6H).

EXAMPLE 23

Synthesis of 4-(4-hydroxy-benzyl)-6,7-dimethoxy-2H-phthalazin-1-one (Compound 7)

A solution of 3-(4-hydroxy-benzyliden)-5,6-dimethoxy-3H-isobenzofuran-1-one (0.3 g, 1 mmole), obtained as described in example 22, and hydrazine (176 μl, 3 mmoles) in methylene chloride (10 ml), under nitrogen, was kept for 3 hours under reflux, then diluted with water, cooled, filtered and the filtrate was dried at warm to give 120 mg of the title compound (yield: 38.46%).

$^1$H-NMR (200 MHz, CDCl$_3$) δ (ppm): 12.37 (s, 1H); 9.24 (s, 1H); 7.27 and 7.25 (2s, 3H) 7.14–6.64 (m, 4H); 4.13 (s, 2H); 3.89 and 3.83 (2s, 6H).

EXAMPLE 24

Synthesis of 3-furan-2-yl-methylen-5,6-dimethoxy-3H-isobenzofuran-1-one

A solution of (5,6-dimethoxy-3-oxo-1,3-dihydro-isobenzofuran-1-yl)-triphenylphosphonium bromide (1 g, 1.87 mmoles), obtained as described in example 12, furfural (180 mg, 1.87 mmoles) and triethylamine (263 μl, 1.87 mmoles) in CH$_2$Cl$_2$ (20 ml), under nitrogen, was kept for 1 night at room temperature, washed with water, dried and brought to dryness. The residue was taken up with ethanol and kept under reflux for 3 hours, cooled, filtered and dried under vacuum to give 250 mg of the title compound (yield: 49.2%).

EXAMPLE 25

Synthesis of 4-furan-2-ylmethyl-6,7-dimethoxy-2H-phthalazin-1-one (Compound 8)

A solution of 3-furan-2-yl-methylen-5,6-dimethoxy-3H-isobenzofuran-1-one (2.7 g, 9.9 mmoles), obtained as described in example 24, and hydrazine (1.46 ml, 30 mmoles) in methanol (30 ml), under nitrogen, was kept under reflux for 4 hours, then cooled, diluted with water, filtered and the filtrate was dried under vacuum to give 1.9 g of the title compound (yield: 67%).

$^1$H-NMR (200 MHz, CDCl$_3$) δ (ppm): 10.30 (s, 1H); 7.77 (s, 1H); 7.14 (s, H); 7.32–6.10 (m, 3H); 4.26 (s, 2H); 4.01 and 3.93 (2s, 6H).

EXAMPLE 26

Synthesis of 1-chloro-4-furan-2-ylmethyl-6,7-dimethoxy-phthalazine

A solution of 4-furan-2-ylmethyl-6,7-dimethoxy-2H-phthalazin-1-one (2 g, 7 mmoles), obtained as described in example 25, and POCl$_3$ (7 ml, 70 mmoles) in acetonitrile (20 ml), under nitrogen, was kept under reflux for 3 hours, then brought to dryness, taken up with methylene chloride, washed with a NaHCO$_3$ solution then with water, dried and brought to dryness. The crude was chromatographed (eluent: benzene:ethyl acetate 7:3 then 1:1) to give 1.3 g of the title compound (yield: 60.7%).

$^1$H-NMR(200 MHz, CDCl$_3$) δ (ppm): 7.46 and 7.35 (2s, 3H); 7.30–6.10 (m, 3H) 4.62 (s, 2H); 4.07 and 3.98 (2s, 6H).

EXAMPLE 27

Synthesis of 1-furan-2-ylmethyl-6,7-dimethoxy-4-phenyl-phthalazine (Compound 9)

A 2M solution of phenyl-lithium (4.27 ml, 8.55 mmoles) in cyclohexane/ethyl ether 7:3 was added dropwise into a 0.5M solution of zinc chloride in anhydrous THF (20 ml, 8.9 mmoles) at 0–5° C. The mixture was kept at room temperature for 1 hour, then 1-chloro-4-furan-2-ylmethyl-6,7-dimethoxy-phthalazine (1.3 g, 4.27 mmoles), obtained as described in example 26, palladium acetate (20 mg, 0.0855 mmoles) and triphenyl-phosphine (45 mg, 0.17 mmoles) were sequentially added. The mixture was kept under reflux for 1 hour, then cooled, diluted with ethyl acetate, washed with a NH$_4$Cl solution, then with water, dried and brought to dryness. The residue was chromatographed (eluent: methylene chloride/methanol 95:4) then crystallised from ethyl ether and dried under vacuum to give 0.9 g of the title compound (yield: 61%).

$^1$H-NMR (200 MHz, CDCl$_3$) δ (ppm): 7.75–6.14 (m, 11H); 4.72 (s, 2H); 4.00 and 3.87 (2s, 6H).

EXAMPLE 28

Synthesis of 3-benzyloxy-4-methoxy-benzaldheyde

A solution of isovanillin (100 g, 0.657 moles) in ethanol (300 ml), potassium carbonate (108.9 g, 0.788 moles), benzyl chloride (86.8 ml, 0.755 moles) and NaI (5 g) under nitrogen was kept under reflux under stirring for 2.5 hours, then cooled, added with water (900 ml). The precipitate was filtered and washed with water, then with petrolatum, then dried under vacuum at 40° C. to give 159 g of the title compound which was used as such in the subsequent step.

EXAMPLE 29

Synthesis of 3-benzyloxy-4-methoxy-benzoic acid

A solution of potassium permanganate (103.83 g, 0.657 moles) in water (1.4 l) was fast added under stirring to a solution of tetrabutylammonium bromide (218.37 g, 0.657 moles) in water (800 ml). The stirring went on for 30 minutes then the precipitate was filtered, washed with water, squeezed and dissolved in pyridine (980 ml) and the solution was dropped into one of 3-benzyloxy-4-methoxy-benzaldheyde (159 g, 0.657 moles), obtained as described in example 28, in pyridine (400 ml), under stirring with water/ice cooling. After standing overnight, the mixture was evaporated and the residue taken up with water (3 l) and acidified with concentrated HCl (500 ml) keeping the temperature around 20° C. with ice. At the end it was kept under stirring for 30 minutes then filtered. The filtrate was treated with ethyl acetate/methanol 1:1 (3 l) under stirring for 30 minutes at 40–50° C., then filtered and the mother liquors were brought to small volume. A crystalline product was obtained, filtered and washed with ethyl acetate and petrolatum to give 139.75 g of the title compound (yield: 82%).

EXAMPLE 30

Synthesis of 3-benzyloxy-4-methoxy-benzoyl chloride

3-Benzyloxy-4-methoxy-benzoic acid (136.84 g, 0.53 moles), obtained as described in example 29, and thionyl chloride (572 ml) were kept under reflux and after 2 hours cooled and evaporated. The residue was taken up several times with toluene to give 148.4 g of the title compound (quantitative yield).

EXAMPLE 31

Synthesis of 3-benzyloxy-N,N-diethyl-4-methoxy-benzamide

A solution of diethylamine (548 ml, 5.3 moles) in CH$_2$Cl$_2$ (452 ml) was added dropwise to a solution of 3-benzyloxy-4-methoxy-benzoyl chloride (146.66 g, 0.53 moles), obtained as described in example 30, in methylene chloride (640 ml), at 0° C. under nitrogen, at constant temperature. At the end the temperature was left to arise to the room value. After 2 hours the mixture was evaporated, taken up with ethyl acetate and washed with water. The organic phase was dried and concentrated to give a solid which, triturated twice with heptane and once with petrolatum, then dried at 45° C. under vacuum gave 150.62 g of the title compound (yield: 91%).

EXAMPLE 32

Synthesis of 3-benzyloxy-N,N-diethyl-2-formyl-4-methoxy-benzamide 1.3 M sec-butyl-lithium in cyclohexane/hexane (54 ml, 0.07 moles) was dropped into a solution under nitrogen of 3-benzyloxy-N,N-diethyl-4-methoxy-benzamide (20 g, 0.064 moles), obtained as described in example 31, tetramethylethylendiamine (10.56 ml, 0.07 moles) in THF (2.25 l) under stirring in a dry ice bath at −70° C. After 2 hours at constant temperature, DMF (21.75 ml, 0.28 moles) was added. The temperature was kept constant for 4 hours then left overnight. The mixture was poured into a NaH$_2$PO$_4$/Na$_2$HPO$_4$ buffer solution (1 l) at pH=7, the phases were separated, the organic one was washed with water (1 l), dried and brought to dryness. The crude was chromatographed (eluent: benzene:ethyl acetate 1:1) to give 6 g of the title compound (yield: 27.4%).

EXAMPLE 33

Synthesis of 5-benzyloxy-6-methoxy-2H-phthalazin-1-one

Hydrazine (8.54 ml, 175 mmoles) was dropped into glacial acetic acid (250 ml) at 0–10° C. and 3-benzyloxy-N,N-diethyl-2-formyl-4-methoxy-benzamide (13 g, 38 mmoles), obtained as described in example 32, was added. The mixture was kept standing for 2 hours, then evaporated, dissolved in CH$_2$Cl$_2$, washed with water, dried with Na$_2$SO$_4$, evaporated to dryness, and the crude was triturated with benzene/ethyl ether 2:1 (150 ml), filtered, washed with benzene and dried under vacuum to give 7 g of the title compound (yield: 78%).

$^1$H-NMR (200 MHz, CDCl$_3$) δ (ppm): 10.61(s, 1H); 8.30(s, 1H); 8.18–7.31(m, 7H); 5.17(s, 2H); 4.03(s, 3H).

EXAMPLE 34

Synthesis of 5-hydroxy-6-methoxy-2H-phthalazin-1-one

A solution of 5-benzyloxy-6-methoxy-2H-phthalazin-1-one (4 g, 14.16 moles), obtained as described in example 33, in concentrated HCl (40 ml) and glacial acetic acid (40 ml) was heated at 60° C. for 1.5 hours, then brought to dryness, taken up with acetone, brought again to dryness and taken up with further acetone, then kept under stirring for 30 minutes, filtered and the precipitate was dried under vacuum at 30° C. to give 2.7 g of the title compound (yield: 99.2%).

$^1$H-NMR (200 MHz, DMSO) δ (ppm): 12.33 (broad signal, 1H); 10.06 (s, 1H); 8.36 (s, 1H); 7.68 and 7.49 (2d, 2H, JHH=8.6Hz); 3.94 (s, 3H).

EXAMPLE 35

Synthesis of 6-methoxy-5-(tetrahydro-furan-2-yloxy)-2H-phthalazin-1-one

3-Mesyloxy-tetrahydrofuran (3.5 g, 21 mmoles) was added to a solution under stirring and nitrogen at room temperature of 5-hydroxy-6-methoxy-2H-phthalazin-1-one (2.7 g, 14 mmoles), obtained as described in example 34, and Na$_2$CO$_3$ (3 g, 28 mmoles), in anhydrous DMF (50 ml).

The mixture was heated at 90° C. for 1 night, then poured into water, extracted twice with ethyl acetate, the organic phase was washed three times with water, dried and brought to dryness. The residue was taken up with ethyl ether (50 ml), triturated under stirring, filtered and dried under vacuum to give 2.1 g of the title compound (yield: 57.2%).

$^1$H-NMR (200 MHz, CDCl$_3$) δ (ppm): 10.9 (s, 1H); 8.42 (s, 1H); 8.15 (d, 1H, JHH=9.2 Hz); 7.36 (d, 1H); 5.25–5.2 (m, 1H); 4.16–3.73 (m, 4H); 3.98 (s, 3H); 2.27–1.98 (m, 2H).

EXAMPLE 36

Synthesis of 6-hydroxy-5-(tetrahydro-furan-2-yloxy)-2H-phthalazin-1-one

A solution of 6-methoxy-5-(tetrahydro-furan-2-yloxy)-2H-phthalazin-1-one (680 mg, 2.6 mmoles), obtained as described in example 35, in DMF (15 ml) and sodium p-thiocresol (378.6 mg, 2.6 mmoles) was heated at 90° C. for 10 hours, poured into water, acidified at pH 6–7 with 1N HCl, evaporated to dryness, taken up with water and brought again to dryness. The crude was chromatographed (eluent: methylene chloride/methanol 9:1) to give 330 mg of the title compound (yield: 52%).

$^1$H-NMR (200 MHz, DMSO) δ (ppm): 12.41 (s, 1H); 11.07 (broad-s, 1H); 8.23 (s, 1H); 7.82 (d, 1H, JHH=8.8Hz); 7.44 (d, 1H); 5.25–5.20 (m, 1H); 4.03–3.59 (m, 4H); 2.11–2.00 (m, 2H).

EXAMPLE 37

Synthesis of 6-difluoromethoxy-5-(tetrahydro-furan-2-yloxy)-2H-phthalazin-1-one

6-Hydroxy-5-(tetrahydro-furan-2-yloxy)-2H-phthalazin-1-one (320 mg, 1.29 mmoles), obtained as described in example 36, in anhydrous DMF (80 ml) and K$_2$CO$_3$ (267 mg, 1.93 moles) were treated with Freon-22 (5 g, 58 mmoles) at 0.5 bar. The mixture was brought to 115° C. for 1 night, then to dryness and chromatographed (eluent: benzene:ethyl acetate 1:1, then ethyl acetate only) to give 300 mg of the title compound (yield: 78%).

$^1$H-NMR (200 MHz, CDCl$_3$) δ (ppm): 10.62 (s, 1H); 8.44 (s, 1H); 8.16 (d, 1H, JHH=9.2 Hz); 7.55 (d, 1H); 6.63 (t, 1H, JHF=72 Hz); 5.24–5.18 (m, 1H); 4.18–3.75 (m, 4H) 2.29–2.09 (m, 2H).

EXAMPLE 38

Synthesis of 1-chloro-6-difluoromethoxy-5-(tetrahydro-furan-2-yloxy)-phthalazine A solution of 6-difluoromethoxy-5-(tetrahydro-furan-2-yloxy)-2H-phthalazin-1-one (280 mg, 0.94 mmoles), obtained as described in example 37, and POCl$_3$ (1.2 ml) was heated at 90° C. for 1.5 hours, then brought to dryness, taken up with methylene chloride, washed with an NaHCO$_3$ saturated solution, then twice with water, dried and brought to dryness to give 296 g of the title compound (yield: 99.7%).

EXAMPLE 39

Synthesis of 1-(3,5-dichloro-pyridin-4-ylmethyl)-6-difluoromethoxy-5-(tetrahydro-furan-2-yloxy)-phthalazine To a solution under nitrogen of 3,5-dichloro-4-methyl-pyridine (457 mg, 2.82 mmoles) in anhydrous DMF (10 ml) was portionwise added 60% NaH (113 mg, 2.82 mmoles) and, after 1 hour at room temperature, 1-chloro-6-difluoromethoxy-5-(tetrahydro-furan-2-yloxy)-phthalazine (296 mg, 0.937 mmoles), obtained as described in example 38, in anhydrous DMF was dropwise added at a temperature <10° C. After 2 hours at room temperature the mixture was poured into a 0.4M buffer solution at pH=7 (50 ml), extracted with ethyl acetate (2×50 ml) and the organic phase was washed with water, dried and concentrated under vacuum. The residue was chromatographed (eluent: benzene:ethyl acetate 1:1, then ethyl acetate only) and then crystallised from ethyl ether/benzene to give 180 mg of the title compound (yield: 43.5%).

$^1$H-NMR (200 MHz, CDCl$_3$) δ (ppm): 9.72 (s, 1H); 8.52 (s, 2H); 7.96 (d, 1H, JHH=9.2 Hz); 7.80 (d, 1H); 6.68 (t, 1H, JHF=74 Hz); 5.34–5.29 (m, 1H); 4.91 (s, 2H); 4.22–3.81 (m, 4H); 2.33–2.08 (m, 2H).

EXAMPLE 40

Synthesis of 1-(3,5-dichloro-pyridin-4-ylmethyl)-3-methansulphonyl-6-difluoromethoxy-5-(tetrahydro-furan-2-yloxy)-4H-phthalazine (Compound 10)

A solution of 1-(3,5-dichloro-pyridin-4-ylmethyl)-6-difluoromethoxy-5-(tetrahydro-furan-2-yloxy)-phthalazine (190 mg, 0.43 mmoles), obtained as described in example 39, in THF (50 ml) was hydrogenated in Parr in the presence of PtO$_2$ (15 mg) for 24 hours. The mixture was filtered and brought to dryness and the residue was dissolved in methylene chloride (10 ml). Triethylamine (0.179 ml, 1.29 mmoles) and CH$_3$SO$_2$Cl (0.1 ml, 1.29 mmoles) were added to the solution. After 1 hour the mixture was washed with water, dried on Na$_2$SO$_4$ and brought to dryness. The residue was chromatographed (eluent: methylene chloride with 2% methanol) and crystallised from ethyl ether (5 ml), filtered and dried under vacuum at 40° C. to give 102 mg of the title compound (yield: 45%).

$^1$H-NMR (200 MHz, CDCl$_3$) δ (ppm): 8.49 (s, 2H); 7.29 and 7.21 (2d, 2H, JHH=8.2 Hz); 6.55 (t, 1H, JHF=73.3Hz); 5.08–5.01 (m, 1H); AB system: Va=4.63, Vb=4.40, JAB=13.7Hz; AB system: Va=4.35, Vb=4.30, JAB=16.5Hz; 4.13–3.73 (m, 4H); 2.76 (s, 3H); 2.18–2.05 (m, 2H).

EXAMPLE 41

PDE 4 enzyme inhibition

Human polymorphonuclear leukocyte isolation

The polymorphonuclear leukocytes (PMNs) were isolated from peripheral blood of healthy volunteers according to Boyum A. (Scand. J. Immunol., 1976, 5th suppl., 9). Briefly, the PMNs were purified by Ficoll-Paque gradient centrifugation followed by sedimentation on dextran and the erythrocyte contamination was eliminated by hypotonic lysis.

PDE 4 enzyme purification

The human PMNs were suspended in TRIS/HCl buffer (10 mM, pH 7.8) containing MgCl$_2$ (5 mM), EGTA (4 mM), mercaptoethanol (5 mM), TRITON-X100 (1%), pepstatin A (1 μM), PMSF (100 μM) and leupeptin (1 μM), and homogenised by Polytron homogeniser. The homogenate was centrifuged at 25,000×g for 30 minutes at 4° C. and the PDE 4 enzyme was purified by ion exchange chromatography using the FPLC technique according to Schudt C. et al. (Naunyn-Schmidberg's Arch. Pharmacol., 1991, 334, 682). The supernatant was seeded on a UNO Q12 column (Bio-Rad) and the enzyme was eluted by sodium acetate linear gradient from 50 mM to 1M using a flow rate of 4.5 ml/minutes. The fractions containing enzymatic activity were pooled, dialysed against water and concentrated. The PDE 4 enzyme was stored at −20° C. in the presence of ethylene glycol (30% v/v) until the use.

PDE 4 activity assay

The enzyme activity was evaluated with a Scintillation Proximity Assay (SPA) kit (Amersham). The enzymatic reaction was performed in a final volume of 100 μl of TRIS/HCl buffer (50 mM, pH7.5), $MgCl_2$ (8.3 mM), EGTA (1.7 mM), cAMP (14M) and [$^3$H]cAMP (100.000 dpm) as tracer. The compounds of the invention, the reference ones or the vehicle were added at different concentrations. As reference compounds 6,7-dimethoxy-4-(pyridin-4-yl-methyl)-2H-phthalazin-1-one (reference 1) and 6,7-dimethoxy-4-(piperidin-4-yl-methyl)-2H-phthalazin-1-one (reference 2) embraced by the general formula of the patent application EP-0 722 936 (in the name of Eisai) were used. The reaction was started by adding 1.5 μg protein and incubated for 40 minutes at 30° C.

SPA beads (50 μl) containing 18 mM zinc sulphate were added to stop the reaction and after 20 minutes at room temperature the radioactivity was measured using a scintillation counter.

The $IC_{50}$ value refers to the nanomolar concentration of the compound required to inhibit cyclic nucleotide hydrolysis by 50%, and it was calculated by non-linear regression analysis.

The compounds of the present invention showed $IC_{50}$ values much lower than those of the comparison: for example, Compound 10 gave a value of $IC_{50}$=8±0.5 nM in comparison with values of $IC_{50}$>100 μM of both the comparison compounds.

What is claimed is:

1. A compound selected from the group consisting of:

N-3-acetyl-1-(3,5-dichloropyridin-4-ylmethyl)-5-cyclopentyloxy-6-methoxy-4H-phthalazine;

6,7-dimethoxy-1-pyridin-4-ylmethyl-4-thiazol-2-yl-phthalazine;

1-(6,7-dimethoxy-4-pyridin-4-ylmethyl-1H-phthalazin-2-yl)ethanone;

2-methanesulphonyl-6,7-dimethoxy-4-pyridin-4-ylmethyl-1,2-dihydrophthalazine;

2-formyl-6,7-dimethoxy-4-pyridin-4-ylmethyl-1,2-dihydrophthalazine;

1-(6,7-dimethoxy-4-pyridin-4-ylmethyl-1H-phthalazin-2-yl)-1-imidazol-1-ylmethanone;

1-(3,5-dichloro-pyridin-4-ylmethyl)-3-methansulphonyl-6-difluoromethoxy-5-(tetrahydro-furan-2-yloxy)-4H-phthalazine;

N→O derivatives thereof; and pharmaceutically acceptable salts thereof.

2. The compound according to claim 1, wherein said compound is N-3-acetyl-1-(3,5-dichloropyridin-4-ylmethyl)-5-cyclopentyloxy-6-methoxy-4H-phthalazine.

3. The compound according to claim 1, wherein said compound is 6,7-dimethoxy-1-pyridin-4-ylmethyl-4-thiazol-2-yl-phthalazine.

4. The compound according to claim 1, wherein said compound is 1-(6,7-dimethoxy-4-pyridin-4-ylmethyl-1H-phthalazin-2-yl)ethanone.

5. The compound according to claim 1, wherein said compound is 2-methanesulphonyl-6,7-dimethoxy-4-pyridin-4-ylmethyl-1,2-dihydrophthalazine.

6. The compound according to claim 1, wherein said compound is 2-formyl-6,7-dimethoxy-4-pyridin-4-ylmethyl-1,2-dihydrophthalazine.

7. The compound according to claim 1, wherein said compound is 1-(6,7-dimethoxy-4-pyridin-4-ylmethyl-1H-phthalazin-2-yl)-1-imidazol-1-yl methanone.

8. The compound according to claim 1, wherein said compound is 1-(3,5-dichloro-pyridin-4-ylmethyl)-3-methansulphonyl-6-difluoromethoxy-5-(tetrahydro-furan-2-yloxy)-4H-phthalazine.

9. A pharmaceutical composition, comprising a therapeutically effective amount of the compound according to claim 1 in admixture with a pharmaceutically acceptable carrier.

* * * * *